US007661178B2

(12) United States Patent
Israel et al.

(10) Patent No.: US 7,661,178 B2
(45) Date of Patent: *Feb. 16, 2010

(54) FASTENER ADAPTER

(75) Inventors: James Israel, Somerset, NJ (US); Eric Heiberg, Long Valley, NJ (US)

(73) Assignee: EBI, LLC, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/212,866

(22) Filed: Sep. 18, 2008

(65) Prior Publication Data

US 2009/0007398 A1 Jan. 8, 2009

Related U.S. Application Data

(63) Continuation of application No. 11/293,685, filed on Dec. 2, 2005, now Pat. No. 7,451,531.

(51) Int. Cl.
*A44B 18/00* (2006.01)
(52) U.S. Cl. ...................................................... 24/442
(58) Field of Classification Search ................. 24/31 V, 24/16 R, 442, 306; 128/DIG. 15; 428/100
See application file for complete search history.

(56) References Cited

U.S. PATENT DOCUMENTS

| 3,461,511 | A | 8/1969 | Perina |
| 4,656,767 | A | 4/1987 | Tarrant |
| 4,862,563 | A | 9/1989 | Flynn |
| 4,893,381 | A | 1/1990 | Frankel |
| 5,008,987 | A | 4/1991 | Armour, II |
| 5,076,288 | A | 12/1991 | Millard et al. |
| 5,136,759 | A | 8/1992 | Armour, II |
| 5,167,050 | A | 12/1992 | Korsen |
| 5,222,765 | A | 6/1993 | Pileggi |
| 6,049,953 | A | 4/2000 | McCay et al. |
| 6,568,981 | B1 | 5/2003 | Chang |
| 7,451,531 | B2 * | 11/2008 | Israel et al. ................... 24/442 |
| 2003/0150087 | A1 * | 8/2003 | Dieterich ....................... 24/306 |

FOREIGN PATENT DOCUMENTS

| EP | 0761184 | 3/1997 |
| JP | 08278753 | 10/1996 |

OTHER PUBLICATIONS

European Search Report of Mar. 13, 2007 for EP06125216.

* cited by examiner

*Primary Examiner*—James R Brittain
(74) *Attorney, Agent, or Firm*—Harness, Dickey

(57) ABSTRACT

A fastener adapter and fastener strap combination includes a first strap member having first and second ends, an outer surface and an inner surface with hook material; and a second strap member having first and second opposing surfaces of hook material. The second strap member is attached to the inner surface intermediately between the first and second ends of the first strap member. The first surface of the second member and a portion of the inner surface of the first member define a first all-hook opening. The second surface of the second member and a portion of the inner surface of the first member define a second all-hook surface. The combination also includes a continuous fastener strap having first and second end portions, the first end portion frictionally attached to the first all-hook opening and the second end portion frictionally attached to the second all-hook surface.

16 Claims, 3 Drawing Sheets

FASTENER ADAPTER

CROSS-REFERENCE TO RELATED APPLICATIONS

This application is a continuation of U.S. patent application Ser. No. 11/293,685 filed on Dec. 2, 2005. The disclosure of the above application is incorporated herein by reference.

INTRODUCTION

Various friction-based fastening systems, such as systems of hook-and-loop straps, are used for restraining or providing adjustable attachments of various external alignment or support devices, such as leg, arm, hand, braces and other medical or orthopedic devices.

Although the existing fastener systems can be satisfactory for their intended purposes, there is still a need for fastener adapters that can be easily and adjustably used with various fastening systems.

SUMMARY

The present teachings provide a fastener adapter for connecting fastener straps. The fastener adapter includes a first strap member having first and second ends, and a second strap member attached to the first strap member intermediately between the first and second ends of the first strap member. The first strap member has an inner surface that includes hook-type material. The second strap member has first and second opposing surfaces that include hook-type material.

The present teachings also provide a fastener adapter that includes an outer member, and an inner member attached at an angle to the outer member such that the outer and inner members cooperate to form first and second pockets. Each of the first and second pockets provides a pair of attachment surfaces that are both of the same type of frictional attachment material.

In another aspect, the present teachings provide a fastener adapter that includes an outer member, and an inner member attached at an angle to the outer member such that the outer and inner members cooperate to form first and second pockets, and at least one of the first and second pockets defines one of an all-hook and an all-loop pocket.

The present teachings provide a fastener adapter and fastener strap combination that includes an outer member, and an inner member attached at an angle to the outer member such that the outer and inner members cooperate to form first and second openings. The first and second openings providing first and second attachment surfaces that are both of the same type of frictional attachment material, wherein the frictional attachment type material is one of loop or hook material. The combination further includes one or more fastener straps comprising complementary frictional attachment material for attachment to the frictional material of the first and second openings.

Further, the present teachings provide a fastener adapter and fastener strap combination includes a first strap member having first and second ends, an outer surface and an inner surface with hook material; and a second strap member having first and second opposing surfaces of hook material. The second strap member is attached to the inner surface intermediately between the first and second ends of the first strap member. The first surface of the second member and a portion of the inner surface of the first member define a first all-hook opening. The second surface of the second member and a portion of the inner surface of the first member define a second all-hook surface. The combination also includes a continuous fastener strap having first and second end portions, the first end portion frictionally attached to the first all-hook opening and the second end portion frictionally attached to the second all-hook surface.

The present teachings also provide a fastener adapter that includes an outer member, and an inner member attached at an angle to the outer member such that the outer and inner members cooperate to form first and second openings. The first opening has first and second opposing attachment surfaces with all-hook frictional attachment material and the second opening defines a third all-hook attachment surface.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DESCRIPTION OF VARIOUS EMBODIMENTS

The following description is merely exemplary in nature and is in no way intended to limit the invention, its application, or uses.

Figure 1:
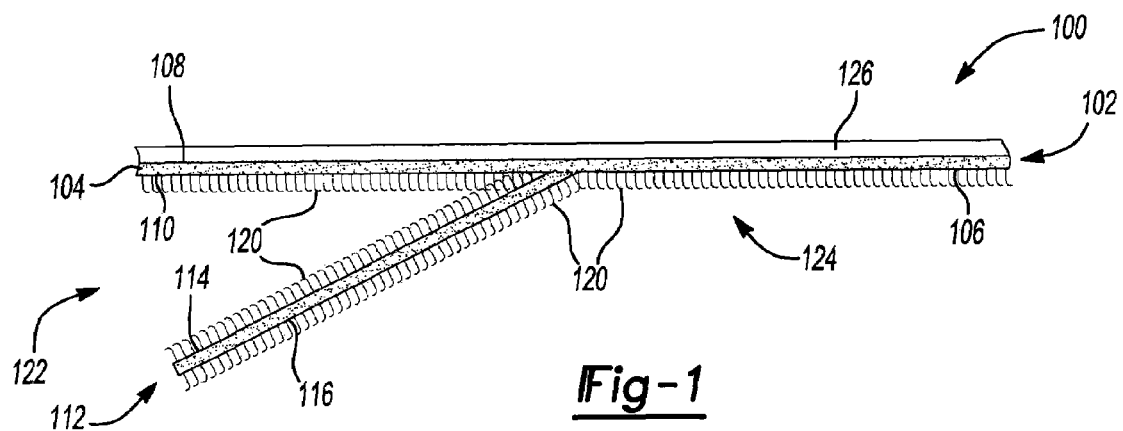
FIG. 1 is a side view of a fastener adapter according to the present teachings.

Referring to FIG. 1, an exemplary fastener adapter 100 is illustrated according to the present teachings. The fastener adapter 100 can include a first strap member 102 having first and second ends 104, 106, and inner surface and outer surfaces 110, 108. The fastener adapter 100 can also include a second strap member 112 having first and second opposing surfaces, 114, 116.

Figure 1A:
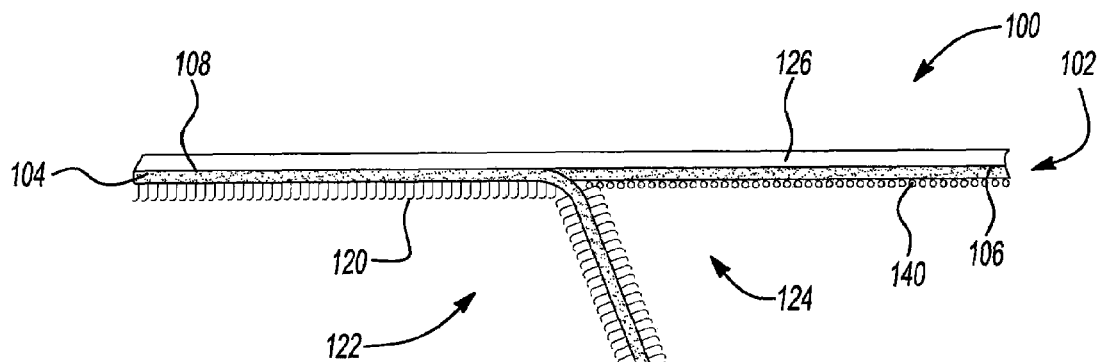
FIG. 1A is a side view of a fastener adapter according to the present teachings.
Figure 1B:
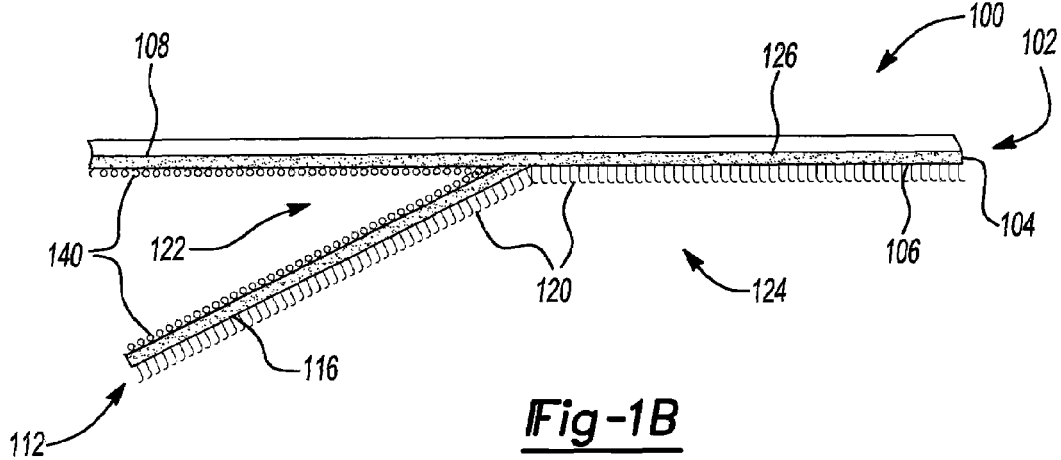
FIG. 1B is a side view of a fastener adapter according to the present teachings.
Figure 1C:
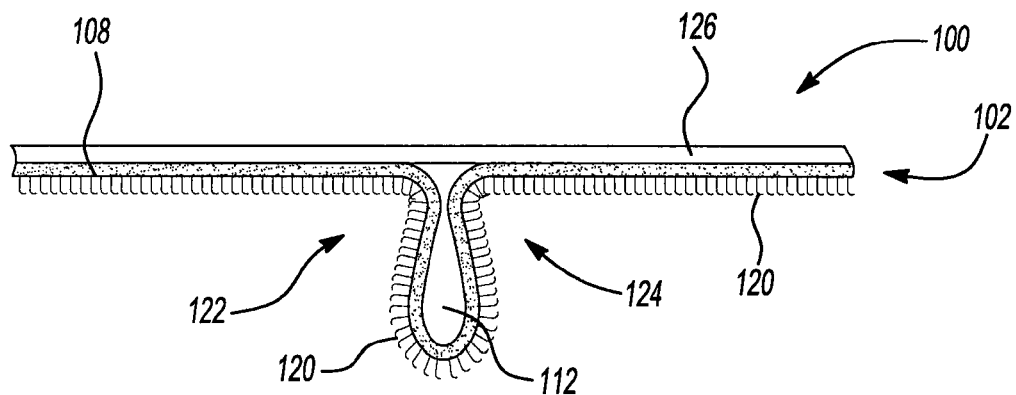
FIG. 1C is a side view of a fastener adapter according to the present teachings.

Referring to FIGS. 1, 1A, and 1B the second strap member 112 can be attached to the inner surface 110 of the first strap member 102 intermediately between the first and second ends 104, 106 of the first strap member 102, and at an angle relative to the first strap member 102. Referring to FIG. 1C, the second strap member 112 can be integral with the first strap member 102, such that a single continuous strap defines both strap members 102, 112.

Figure 2:
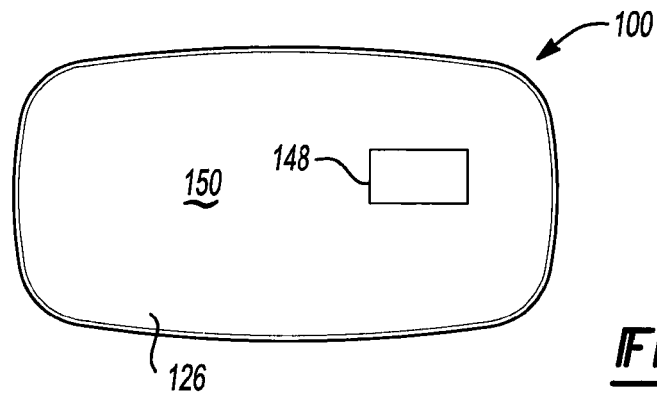
FIG. 2 is a top view of a fastener adapter according to the present teachings.
Figure 3:
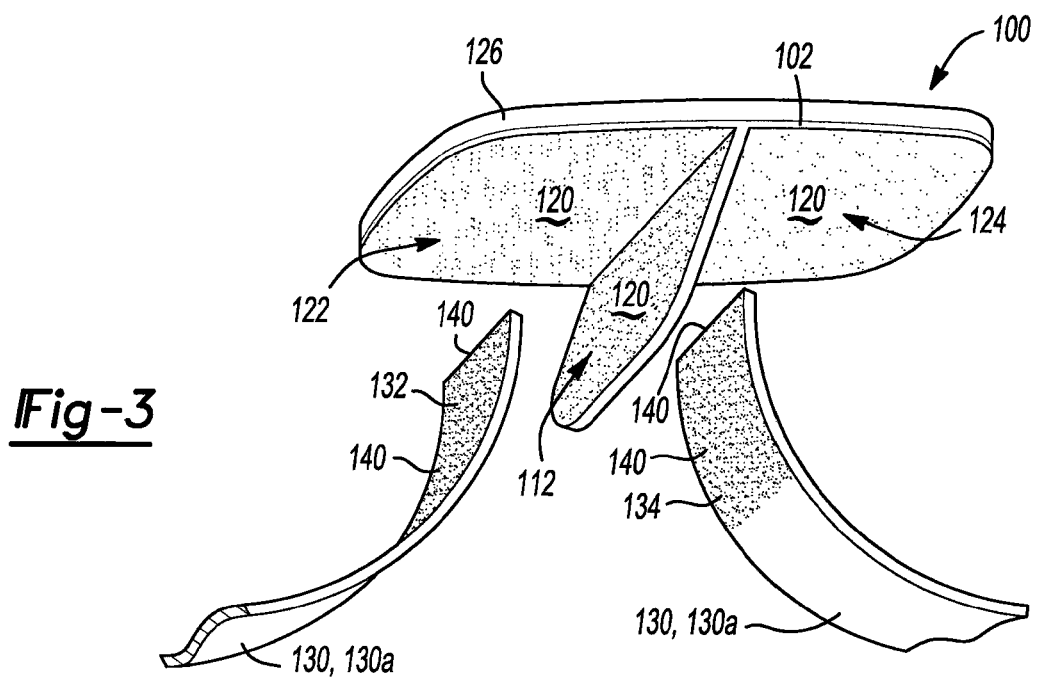
FIG. 3 is a perspective view of a fastener adapter according to the present teachings shown for attachment with one or two fastener straps.

Referring to FIGS. 1-4, the entire inner surface 110 of the first strap member 102 or a portions thereof on each side of the second strap member 112 can include a single type of frictional attachment material, such as, for example, hook-type material 120 suitable for fastening to complementary attachment material, such as loop-type material 140, as in Velcro®, or similar frictional attachment fasteners. Similarly, the first and second surfaces 114, 116 of the second strap member 112 or portions thereof can also include the same type of frictional attachment material, such as hook-type attachment material 120. Referring to FIG. 3, the inner surface 110 of the first strap member 102 can cooperate with the first and second surfaces 114, 116 of the second strap member 112 to define first and second all-hook openings or pockets 122, 124 suitable for attachment with a single continuous strap 130, which includes first and second attachment ends 132, 134, each of which presents a pair of opposite loop attachment surfaces 140. Instead of a single strap 130, two (or more) straps 130a, 130b with corresponding attachment ends 132, 134 can also be used.

Figure 3A:
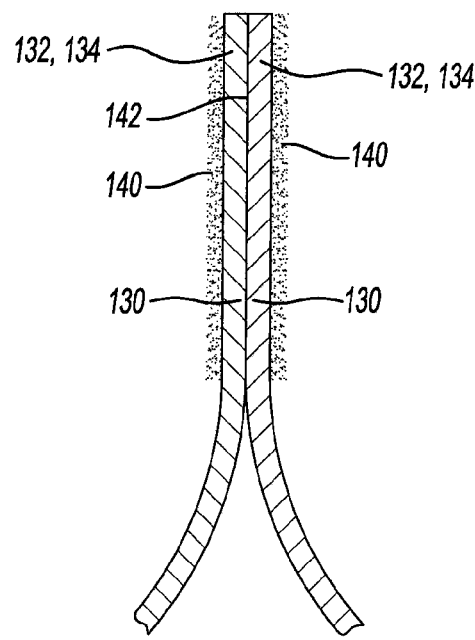
FIG. 3A is a sectional view of a strap for a fastener adapter according to the present teachings.

Referring to FIG. 3A, the continuous strap 130 (or each strap 130a, 130b) can be a double, triple or multiple strap, presenting opposite loop attachment surfaces 140 for attachment with one of the first or second pockets 122, 124, and having opposing inner surfaces 142 which can cooperate for attachment therebetween, for example, by opposing hook and loop surfaces frictionally attached, or by being glued or sewn together at the ends 132, 134. The opposing inner surfaces 142 can also be left completely unattached to each other.

It will be appreciated that the fastener adapter 100 can be used with various combinations of fastener straps 130, 130a, 130b that provide at least one surface of loop material 140. One or more fastener adapters 100 can be used with complex fastening systems, as may be required for various medical fastening/restraining procedures or orthopedic and other medical devices, such arm, leg, foot, hand or other braces that may be worn for various chronic or trauma conditions, including, for example, osteoarthritis pain, fracture support, or correction of various deformities and misalignments.

Referring to FIG. 1, it will be appreciated that the first and second pockets 122, 124 of the fastener adapter 100 can also be made with all loop-type material 140 rather than hook-type material 120 for attachment to fasteners straps 130 that have hook, instead of loop, complementary attachment surfaces. Other combinations of hook and loop materials 120, 140 can be used for the first and second pockets 122, 124, as illustrated in FIGS. 1A-C, such that each of the first and second pockets 122, 124 is an all-hook or an all-loop pocket, or one of the first and second pockets 122, 124 is an all-hook pocket and the other an all-loop pocket, or one of the first and second pockets 122, 124, is of mixed hook and loop material, having opposing surfaces of different (opposite) hook and loop material. For example, referring to FIG. 1A, one of the first and second pockets 122, 124 can be made of all hook material 120 (or all-loop material 140), and the other the first and second pockets 122, 124, can be made of one of each hook and loop material 120, 140. Referring to FIG. 1B, one of the first and second pockets can be made entirely of all-loop material 140 (or all-hook material 120), and the other the first and second pockets 122, 124, can be made entirely of the opposite all-hook 120 (or all-loop material 140). Referring to FIG. 1C, although both pockets 122, 124 are illustrated as made of all-hook material 120, the combination of hook and loop materials 120, 140 discussed above in connection with FIGS. 1A and 1B, can also be used for the fastener adapter 100 illustrated in FIG. 1C.

Figure 4:
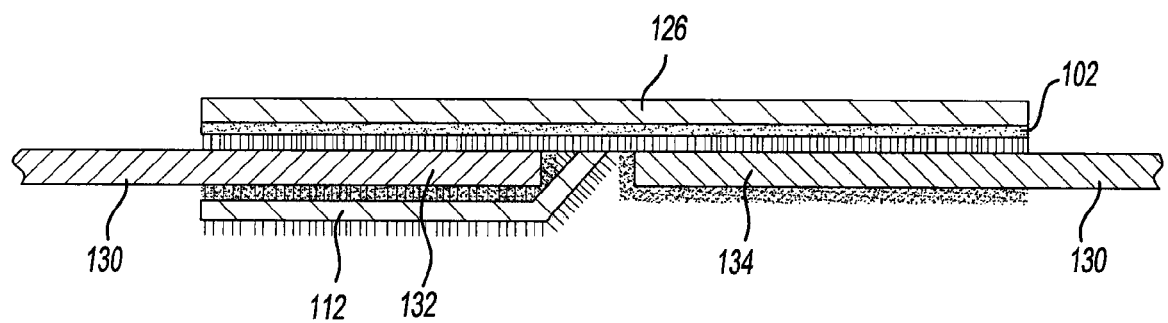
FIG. 4 is a side view of a fastener adapter according to the present teachings shown attached to one or two fastener straps.

The first and second strap members 102, 112 can be tabs or strap portions made from cloth or plastic or other flexible and bendable material to which hook or loop material, as described above, can be attached using adhesive or other bonding or stitching techniques. Furthermore, the fastener adapter 100 can be configured for being substantially flat when connecting two attachment ends 132, 134 of one or more fastener straps 130, as shown in FIG. 4, without substantially adding to the bulk of the fastener straps 130.

Referring to FIGS. 1 and 2, a flexible laminated layer 126 can be attached to the outer surface 108 of the first strap member 102. The laminated layer 126 can include an outer surface 150 which can be embossed or otherwise marked with various indicia 148. The indicia 148 can include, for example, aesthetically pleasing designs and textures, and/or functional markings for brand/source identification, arrows, instructional or other informational markings, and combinations thereof. In this connection, the fastener adapter 100 can be at least partially pre-assembled to one or more fastener straps 130 of a supporting/fixation/restraining device (not shown), such that the indicia 148 provide instructions for completing the connection of the device.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A fastener adapter and fastener strap combination comprising:
 a first strap member having first and second ends, an outer surface and an inner surface, wherein the inner surface comprises hook material; and
 a second strap member having first and second opposing surfaces, the first and second opposing surfaces comprising hook material, the second strap member attached to the inner surface intermediately between the first and second ends of the first strap member, wherein the first surface of the second member and a portion of the inner surface of the first member define a first all-hook opening, and wherein the second surface of the second member and a portion of the inner surface of the first member define a second all-hook surface; and a continuous fastener strap having first and second end portions, the first end portion frictionally attached to the first all-hook opening and the second end portion frictionally attached to the second all-hook surface.

2. The combination of claim 1, further comprising a laminated layer attached to the outer surface of the first member.

3. The combination of claim 2, wherein the laminated layer includes surface indicia.

4. The combination of claim 3, wherein the surface indicia include identification markings.

5. The combination of claim 3, wherein the surface indicia include instruction markings.

6. The combination of claim 1, wherein the first and second strap members of the fastener adapter can lie substantially flat against one another.

7. A fastener adapter and fastener strap combination comprising:
 an outer member;
 an inner member attached at an angle to the outer member such that the outer and inner members cooperate to form first and second openings, the first and second openings providing first and second attachment surfaces that are both of the same type of frictional attachment material, wherein the frictional attachment type material is one of loop or hook material; and one or more fastener straps comprising complementary frictional attachment material for attachment to the frictional material of the first and second openings.

8. The combination of claim 7, wherein the inner member of the fastener adapter can lie substantially flat against the outer member.

9. The combination of claim 7, wherein the outer and inner members are flexible.

10. The combination of claim 7, wherein the outer and inner members are defined from a single integral member.

11. The combination of claim 7 further including a laminated layer attached on an external surface of the outer member.

12. The combination of claim 7, wherein the frictional attachment material is all-hook material.

13. The combination of claim 7, wherein the frictional attachment material is all loop material.

14. A fastener adapter comprising:
an outer member having an outer surface without frictional attachment material and an inner surface with all-hook attachment material; and
an inner member having first and second opposing surfaces, each of the first and second surfaces having all-hook attachment material, the inner member attached at an angle to the outer member, such that a first portion of the inner all-hook attachment surface of the outer member and the first surface of the inner member cooperate to form an opening having first and second opposing attachment surfaces with all-hook frictional attachment material, and such that a second portion of the inner all-hook attachment surface of the outer member and the second surface of the inner member form a third all-hook attachment surface; and
a fastener strap having first and second end portions, the first end portion frictionally attached to the first and second attachment surfaces of the opening, and the second end portion frictionally attached to the third all-hook attachment surface.

15. The fastener adapter of claim 14, wherein the outer surface includes a laminated area.

16. The combination of claim 14, wherein the inner member of the fastener adapter can lie substantially flat against the outer member.

\* \* \* \* \*